United States Patent [19]
Bell

[11] Patent Number: 5,858,194
[45] Date of Patent: Jan. 12, 1999

[54] CAPILLARY, INTERFACE AND HOLDER

[75] Inventor: Michael L. Bell, Fullerton, Calif.

[73] Assignee: Beckman Instruments, Inc., Fullerton, Calif.

[21] Appl. No.: 678,428

[22] Filed: Jul. 18, 1996

[51] Int. Cl.[6] ............................ G01N 27/26; B01D 63/08
[52] U.S. Cl. ............... 204/601; 210/321.75; 210/321.84; 210/455; 422/99; 204/518; 216/2
[58] Field of Search ....................... 138/115; 210/321.75, 210/321.84, 445, 455; 347/65, 71; 204/450, 601, 518; 7/451, 600, 100, 101, 102, 104; 422/99, 81; 216/2; 29/890.1

[56] References Cited

U.S. PATENT DOCUMENTS

| | | | |
|---|---|---|---|
| 4,212,742 | 7/1980 | Solomon et al. | 210/247 |
| 4,228,015 | 10/1980 | De Vries et al. | 210/321.75 |
| 4,891,120 | 1/1990 | Sethi et al. | 204/600 |
| 4,908,112 | 3/1990 | Pace | 210/198.2 |
| 4,935,040 | 6/1990 | Goedert | 55/197 |
| 5,116,495 | 5/1992 | Prohaska | 210/198 |
| 5,165,292 | 11/1992 | Prohaska | 73/866 |
| 5,173,164 | 12/1992 | Egen et al. | 204/301 |
| 5,192,412 | 3/1993 | Kambara et al. . | |
| 5,194,133 | 3/1993 | Clark et al. | 204/608 |
| 5,296,114 | 3/1994 | Manz . | |
| 5,338,427 | 8/1994 | Shartle et al. | 204/299 R |
| 5,348,658 | 9/1994 | Fuchs et al. | 210/656 |
| 5,376,252 | 12/1994 | Ekstrom et al. | 204/299 R |
| 5,453,382 | 9/1995 | Novotny et al. | 436/178 |
| 5,659,346 | 8/1997 | Moynihan et al. | 347/68 |

FOREIGN PATENT DOCUMENTS

| | | |
|---|---|---|
| 0 475 164 A2 | 3/1992 | European Pat. Off. . |
| 0 617 278 A1 | 9/1994 | European Pat. Off. . |
| 43 14755 A1 | 11/1994 | Germany . |
| 4314755A1 | 11/1994 | Germany . |

OTHER PUBLICATIONS

Efenhauser, Carlo S., et al; "Glass Chips fro High–Speed Capillary Electrophoresis Separations with Submicrometer Plate Heights"; Anal. Chem. 1993, 65, pp. 2637–2642.

English language translation of the abstract of Knoll et al. (DE 4314755 A1), Nov. 1994.

definition of "capillary" according to Webster's II—New Riverside University Dictionary, 1994.

*Primary Examiner*—Robert Warden
*Assistant Examiner*—Alex Noguerola
*Attorney, Agent, or Firm*—William H. May; P. R. Harder; Steven G. Roeder

[57] ABSTRACT

A capillary, interface and holder for a capillary electrophoresis system are provided herein. The capillary is disposed in a substantially planar housing having side surfaces. The capillary includes at least two, substantially coplanar capillary openings which extend through an interface surface located on one of the side surfaces. The interface includes at least two spaced apart receptacles for receiving an ionic fluid. Each receptacle includes a liquid permeable medium having a capillary area and a conductor area. Each capillary area is in fluid communication with one of the capillary openings and each conductor area is in contact with at least one electrical conductor. At least two of the capillary areas are substantially coplanar. The ionic fluid is disposed in each receptacle to create an electrical path between the capillary area and conductor area of each receptacle. The holder selectively retains the housing and the interface so that the capillary areas contact the capillary openings and the conductor areas contact the electrical conductors.

38 Claims, 6 Drawing Sheets

CAPILLARY, INTERFACE AND HOLDER

BACKGROUND

1. Field of the Invention

The present invention is directed to a capillary, an interface and a holder for a capillary electrophoresis ("CE") system. In particular, the capillary, interface and holder are useful for planar capillary electrophoresis ("PCE") and related techniques.

2. Description of Related Art

A detailed description of PCE is provided in the article Glass Chips for High Speed Capillary Electrophoresis Separations With Submicrometer Plate Heights by Carlo S. Effenhauser, Andreas Manz and H. Michael Widmer, which was published in *Analytical Chemistry,* Volume 65, Oct. 1, 1993, pages 2637–2642, ("Glass Chips Article"), the contents of which are incorporated herein by reference.

CE and PCE are used in analytical and biomedical research for the rapid separation and analysis of charged species including synthetic polynucleotides, DNA sequencing fragments, DNA restriction fragments, amino acids, ions and the separation of proteins, viruses and bacteria.

CE and PCE typically utilize an electric potential difference to separate and transport components of a sample inside a capillary. A variety of detectors are available for detecting the sample components including uv-visible detection, electrochemical detection and more recently, laser induced fluorescence detection which involves labeling sample components with a fluorescent tag, such as e.g. fluorescein.

Laser induced fluorescence utilizes one or more lasers to illuminate a window section of the capillary. This illumination results in the laser excitation of the fluorescent material within the window section and causes the fluorescent material to emit radiation. These emissions are collected by a collection device and sent to a detector which converts the emission energy to a usable signal for analysis.

PCE utilizes a capillary defined by a network of interconnected, tiny, short channels formed in a planar housing. The network is useful for separating a sample into a small sample plug for testing or for combining or separating various reactants.

PCE has great potential since the small sample plug, used in combination with a short capillary and a high electrical potential allows for fast and efficient separation of the sample constituents with excellent resolution. Further, with PCE, multiple capillaries, each having multiple networks can be manufactured relatively inexpensively into the housing.

However, existing PCE systems are not entirely satisfactory since there is difficulty interfacing or connecting the network of tiny channels to electrical conductors and to samples, reactants or other fluids.

As provided in the Glass Chips Article, one way of interfacing each channel with an electrical conductor and reactant liquids includes drilling a port at the end of each channel. Next, a pipette tip is glued into the port and the pipette tip is filled with an ionic fluid. The electrical conductor is disposed in the ionic fluid.

This method of interfacing has numerous drawbacks. First, individually drilling each port in alignment with a channel and gluing each pipette tip into the port is relatively expensive. Second, a difference in hydrostatic pressure occurs if the height of the ionic fluid is not consistent in each of the pipette tips or the orientation of the housing is changed. The difference in hydrostatic pressure causes unwanted fluid flow in the channels. Thus, the level of fluid in each of the pipette tips must be carefully measured and maintained throughout the experiment to prevent unwanted fluid flow in the channels and the capillary housing must be maintained at the same orientation throughout the experiment.

Third, the test sample and reactants are in fluid communication with each other through the network of channels. Thus, the components can diffuse together and mix causing unwanted reactions or contamination between testing. This can be prevented by the inclusion of valves within the ports. However, this also increases the cost and complexity of the system.

Fourth, dead volumes can exist between the intersection of the pipette tip and the port which are difficult to clean. Thus, there is a risk of contamination and/or erroneous results if existing capillaries are reused.

Accordingly, there is a need for a capillary, an interface and a holder which (i) are relatively easy and inexpensive to manufacture, (ii) are relatively easy to use and clean, and (iii) reduce the potential for diffusion of the components between experiments.

SUMMARY

The present invention is directed to a capillary, an interface, and a holder for a capillary electrophoresis system which meet these needs. A capillary according to the present invention includes a channel disposed in a substantially planar housing and at least one capillary opening which is in fluid communication with the channel. The channel is suitable for transporting a sample during capillary electrophoresis. The capillary opening extends through an interface surface of the housing. The interface surface is located on a side surface of the housing. Preferred capillary embodiments include at least a second capillary opening which is coplanar with the first capillary opening.

As detailed below, the capillary openings interact with the interface disclosed herein, without the need for pipette tips. Further, if the capillary openings extend through the side surface of the housing, the capillary opening can be manufactured simultaneously with the channel. Thus, there is no need for specially drilled ports which must be aligned with the tiny channels.

Each capillary can include a network of interconnected channels and each channel can include a capillary opening which extends through one of the side surfaces of the housing or an alternate surface of the housing. For example, a plurality of capillary openings can extend through the same surface to facilitate interaction with the interface as described below. Additionally, groups of capillary openings can be spaced apart a uniform distance which is substantially equal to "X".

An interface having features of the present invention is useful for interfacing a capillary having a pair of spaced apart capillary openings with externally applied fluids. The interface includes at least two receptacles for receiving ionic fluids with each receptacle including a liquid permeable medium. The receptacles are spaced apart from each other a sufficient distance so that each receptacle can be placed in fluid communication with at least one of the capillary openings. In alternative embodiments the interface includes a capillary area, a conductor area, and an ionic fluid disposed in each receptacle for establishing an electrical path between the capillary area and the conductor area of each receptacle. An electrical path can be established between the capillary area and conductor area of each of the receptacles without establishing an electrical path between at least two receptacles.

Preferably, the receptacles are positioned so that at least two of the capillary areas are substantially coplanar to facilitate interaction with a pair of capillary openings which extend through the same surface of a planar housing.

Typically, the capillary areas are spaced apart so that each of the capillary areas can be connected in fluid communication with one of the capillary openings. For example, if consecutive capillary openings are spaced apart a distance which is substantially equal to "X", the distance between consecutive capillary areas is also substantially equal to "X" so that one of the capillary areas can be connected to each capillary opening.

The interface includes an inhibitor which inhibits the flow of ionic fluid between adjacent receptacles. For example, the receptacles can be made from a single, continuous piece or sheet of liquid permeable medium and the inhibitor can be a hydrophobic barrier such as ink or a gap disposed between the adjacent receptacles which does not contain a liquid permeable medium.

Alternately, the receptacles can be made from a continuous piece or sheet of liquid permeable medium which inhibits the flow of liquid laterally between adjacent receptacles.

The interface can include a support for retaining the receptacles and detachably securing the interface proximate to the capillary opening. Further, the support can include an interface aligner for aligning the interface with the capillary openings.

The ionic fluid is disposed in at least a portion of each receptacle to establish the electrical path between the capillary area and the conductor area of each receptacle. The ionic fluid can be the sample being tested or an alternate fluid, such as a separation buffer or other reactant.

The holder is used to selectively retain the interface in fluid communication with the capillary openings and in contact with the electrical conductors.

The invention also includes a method for making a capillary and a method for interfacing a capillary opening with an electrical conductor and reactant fluids.

Since the capillary openings can be manufactured simultaneously with the channels in the planar housing and the interface is made of a liquid permeable medium, the capillary and the interface are relatively inexpensive to manufacture and are easy to connect and disconnect. Thus, the capillary is relatively easy to clean and can be washed without fear of backwashing into reagent reservoirs.

Additionally, the problems associated with pipette tips, i.e., the diffusion of the components between experiments, the need for valves, the need to maintain the level of fluid in the pipette tips constant and the need to maintain orientation of the capillary are eliminated.

DRAWINGS

These and other features, aspects and advantages of the present invention will become better understood from the following description, appended claims and accompanying drawings where:

DESCRIPTION

Figure 1:
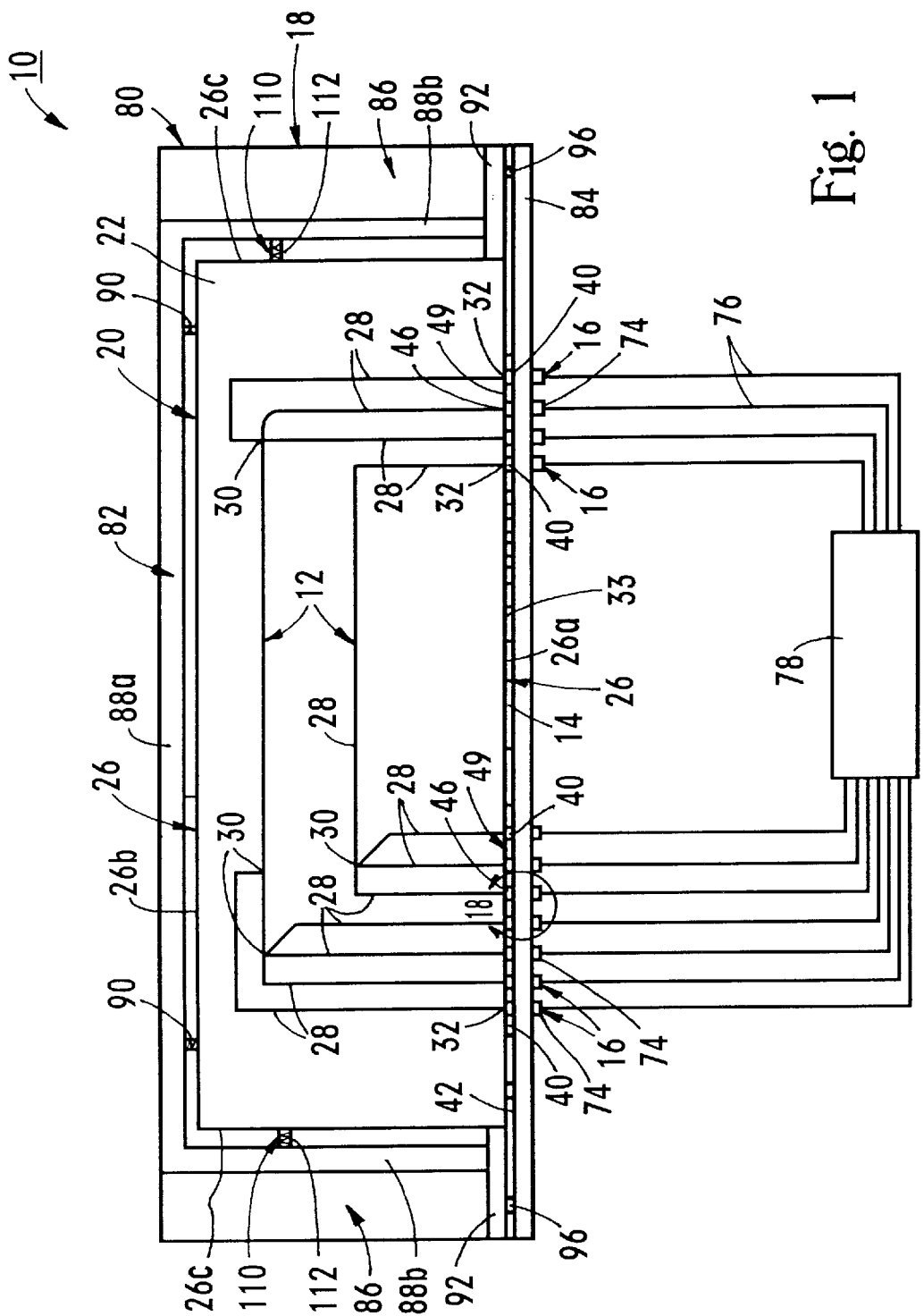
FIG. 1 is a front plan view of a portion of a capillary electrophoresis system having features of the present invention.

With reference to the Figures, a capillary electrophoresis system 10 according to the present invention includes (i) at least one capillary 12; (ii) an interface 14; (iii) a plurality of electrical conductors 16; and (iv) a holder 18.

Coplanar as used herein means lying or acting in the same plane.

The capillary 12 is disposed in a substantially planar housing 20. The dimensions of the housing 20 vary according to the desired design of the capillary 12. In the embodiment shown in the figures, the housing 20 is rectangular and is about one (1) by three (3) by fifteen hundredths (0.15) inches.

The housing 20 includes a front surface 22, an opposed back surface 24 and three or more side surfaces 26. For example, the rectangular shaped housing 20 shown in the figures has four side surfaces 26 including a bottom side surface 26a, a top side surface 26b, and opposed end side surfaces 26c. Alternately, a triangle shaped, planar housing (not shown) would have three side surfaces.

Figure 2:
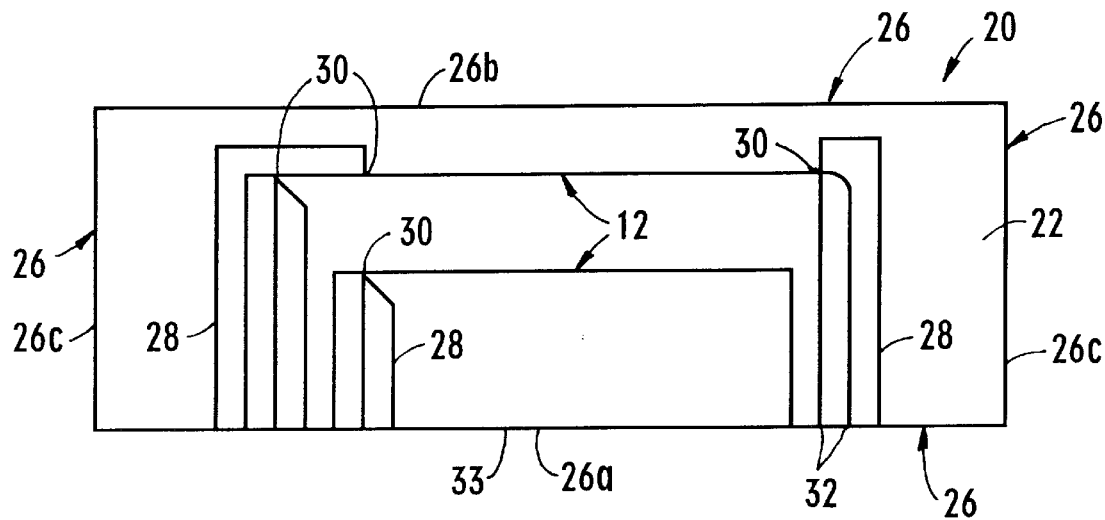
FIG. 2 is a front plan view of a housing having features of the present invention.

The housing 20 can contain two or more capillaries 12. In the embodiment shown in FIG. 2, the housing 20 includes two capillaries 12.

Each capillary 12 can include a plurality of interconnected channels 28 of almost any shape. The interconnected channels 28 form networks 30 which allow for separation of the sample into a small sample plug (not shown) and/or combining or separating various reactants. The number of channels 28 and shape of each capillary 12 varies according to the needs of the experiment.

The dimensions of each channel 28 varies according to the requirements of the experiment. Typically, each of the channels 28 has a cross-sectional area of between about one hundred to five thousand micrometers squared (100–5000 $\mu m^2$).

Each channel 28 can include a capillary opening 32 which extends through an interface surface 33 located on the front surface 22, back surface 24 and/or side surfaces 26 of the housing 20 to allow for connection to the electrical conductors 16. In the embodiment shown in the FIGS. 1–3, the capillary openings 32 extend through the bottom side surface 26a of the housing 20. Alternately, depending upon the design of the CE system 10, some or all of the capillary openings 32 can extend through the top side surface 26b, the front surface 22, the back surface 24 or one of the opposed end side surfaces 26c of the housing 20.

Preferably, all of the capillary openings 32 extend through the same interface surface 33 and are substantially coplanar to facilitate the use of a single interface 14 and for ease of manufacturing the housing 20 as described below.

Typically, each capillary opening 32 has a cross-sectional area and shape which is substantially equal to a cross-sectional area and shape of each channel 28. However, the size and shape of each capillary opening 32 can be larger or smaller depending upon the design of the interface 14. In the embodiment shown in FIG. 3, each capillary opening 32 has a half circular cross-sectional shape. Alternately, the shape of each capillary opening 32 can vary. For example, each capillary opening 32 can have a rectangular or trapezoidal cross-sectional shape.

The distance between the capillary openings 32 varies according to the design of the capillary 12 and the design of the interface 14. In the embodiment shown in the figures, the capillary openings 32 are divided into two groups of evenly spaced capillary openings 32. The distance between consecutive capillary openings 32 in each group is about one-tenth (1/10) of an inch. Alternately, the distance between consecutive capillary openings 32 can vary.

For ease of manufacturing, the housing 20 comprises a channel plate 34 and a cover plate 36. In the embodiment shown in FIG. 3, each capillary 12 includes a plurality of channels 28 formed in an upper surface 38 of the channel plate 34. Alternately, each capillary 12 can be formed in the cover plate 36.

Preferably, each channel 28 extends through one of the side surfaces 26 to form each capillary opening 32 for ease of manufacturing. Thus, the channel 28 and the capillary opening 32 are formed during the same manufacturing process. Alternately, each of the capillary openings 32 can be an aperture (not shown) drilled through the front surface 22 or the back surface 24 into one the channels 28. However, this requires an additional manufacturing step.

Figure 3:
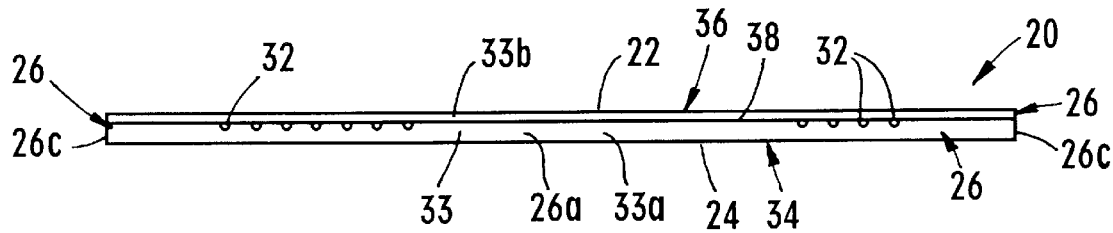
FIG. 3 is a bottom plan view of the housing of FIG. 2.
Figure 4:
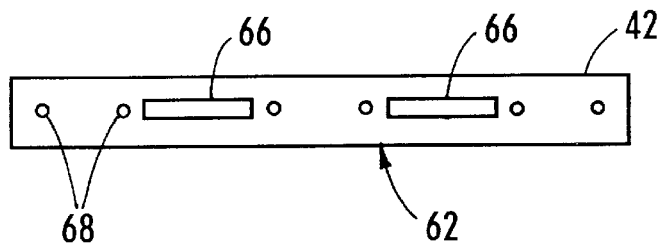
FIG. 4 is a top plan view of a portion of a support having features of the present invention.

Referring to FIG. 3, the cover plate 36 is sealed over the upper surface 38 of the channel plate 34 to form each capillary 12. At least one capillary opening 32 extends through an interface surface 33 located on one of the side surfaces 26, and an interface surface 33a of the channel plate 34 and an interface surface 33b of the cover plate 36 are substantially aligned and retained substantially coplanar during assembly of the channel and cover plates 34, 36. This forms a substantially flat surface which facilitates connection with the interface 14. Alternately, one or more of the side surfaces 26 can be ground or cut to expose the capillary openings 32 and form the flat interface surface 33 for connection with the interface 14. However, grinding or cutting of the side surface 26 can plug the small capillary openings 32.

The channel and cover plates 34, 36 can be manufactured out of a number of materials including glass, plastic or a semi-conductive material such as monocrystalline silicon. Molding, photolithographic procedures or micro-mechanical processing procedures such as wet chemical etching, plasma etching or isotropic etching can be used to form the channels 28 in one of the plates 34, 36.

Assembly of the channel and cover plates 34, 36 varies according to the material utilized in the plates 34, 36. For example, channel and cover plates 34, 36 made from glass can be thermal bonded at a temperature of about six hundred and twenty degrees celsius (620° C.) for about four (4) hours under about one (1) P.S.I. Suitable housings 20 can be manufactured by a number of vendors including Alberta Microelectronic Centre, Alberta, Canada and Baumer IMT Industrielle Messtechnik AG, CH-8606 Greifensee, Switzerland.

Referring to FIGS. 7–10, the interface 14 includes at least two spaced apart receptacles 40 attached to a support 42. Each receptacle 40 comprises a liquid permeable medium and an ionic fluid 44 is disposed in each receptacle 40. The receptacles 40 can include at least one capillary area 46 and at least one conductor area 48 with the ionic fluid creating an electrical path between the capillary area 46 and the conductor area 48.

As provided in detail below, the receptacles 40 are spaced apart and separated by an area which is not saturated by the ionic fluid 44 so that there is no electrical connection between adjacent receptacles 40.

For example, the receptacles 40 can be separated by an inhibitor 49 which inhibits the flow of ionic fluid 44 between the adjacent receptacles 40. In the embodiment shown in FIG. 9, a plurality of receptacles 40 can be made from a continuous piece or sheet of liquid permeable medium and the inhibitor 49 can be a hydrophobic barrier in the liquid permeable medium between adjacent receptacles 40. The hydrophobic barrier can be a flow retarding barrier, such as ink, impregnated into the continuous piece or sheet of liquid permeable medium or a slot in the piece or sheet of liquid permeable medium.

Figure 7:
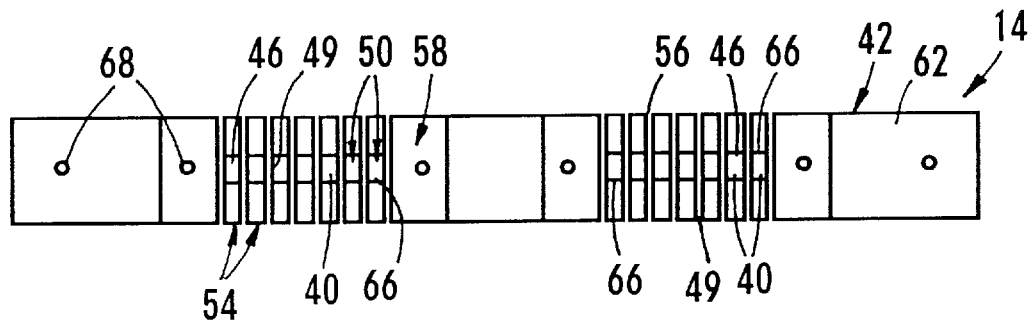
FIG. 7 is a top plan view of an interface having features of the present invention.
Figure 8:
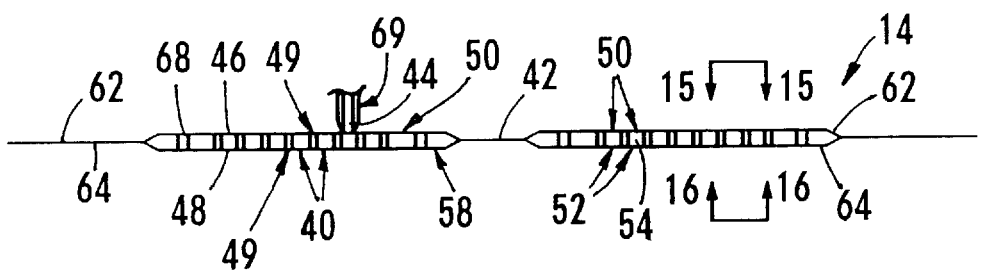
FIG. 8 is a side plan view of the interface of FIG. 7 and a cutaway view of a pipette tip for distributing an ionic fluid onto the interface.
Figure 9:
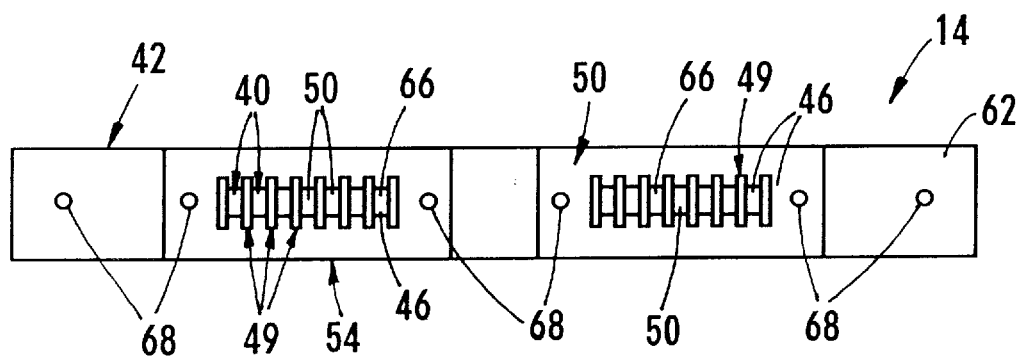
FIG. 9 is a top plan view of a second interface having features of the present invention.

In another embodiment shown in FIGS. 7 and 8, each receptacle 40 can be a small piece or strip of liquid permeable medium and the inhibitor 49 can be a space between the small pieces or strips of liquid permeable medium which does not contain a liquid permeable medium. In this embodiment, each piece or strip of liquid permeable medium is substantially rectangular and planar. Each piece of the liquid permeable medium can alternately be substantially disc shaped or some other shape.

Figure 10:
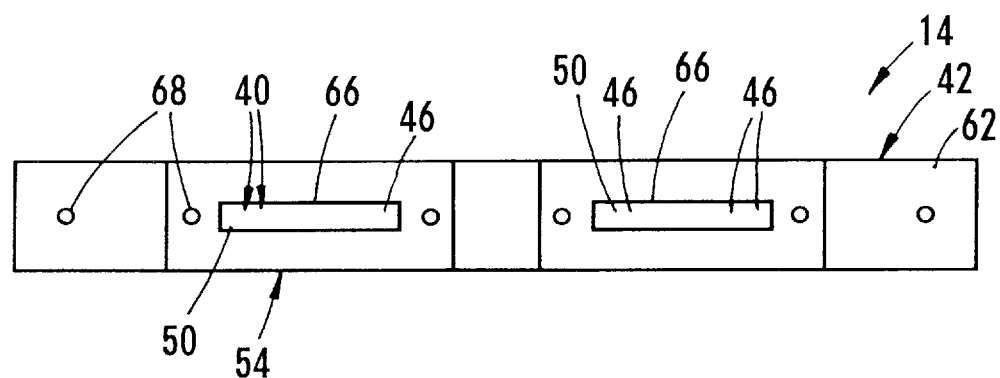
FIG. 10 is a top plan view of a third interface having features of the present invention.
Figure 11:
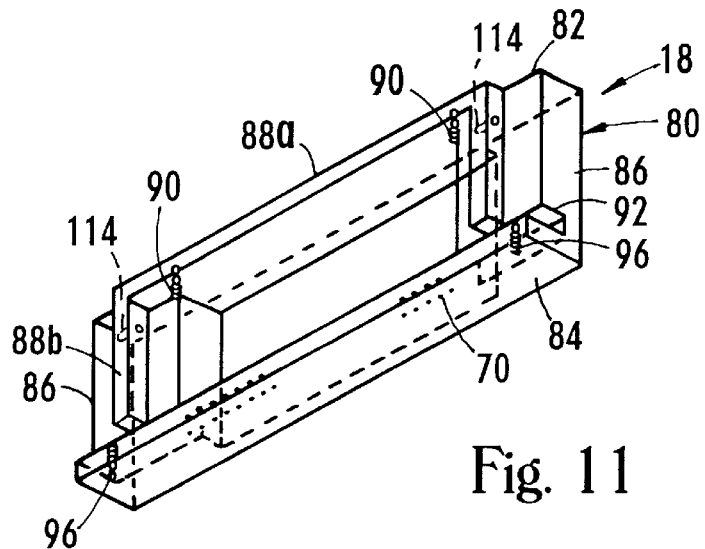
FIG. 11 is a perspective view of a holder having features of the present invention.
Figure 12:
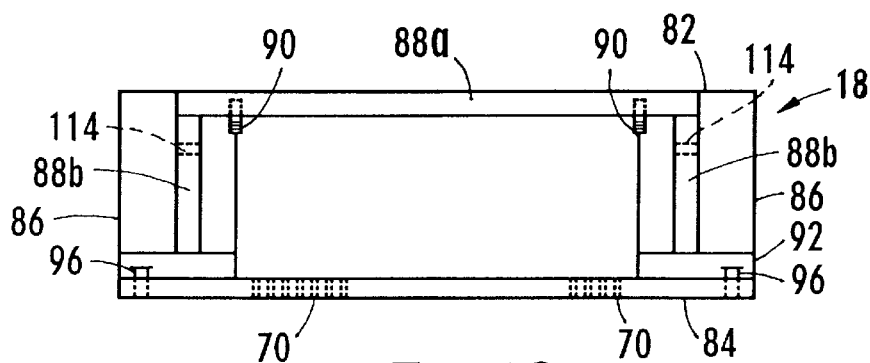
FIG. 12 is a front plan view of the holder of FIG. 11
Figure 13:
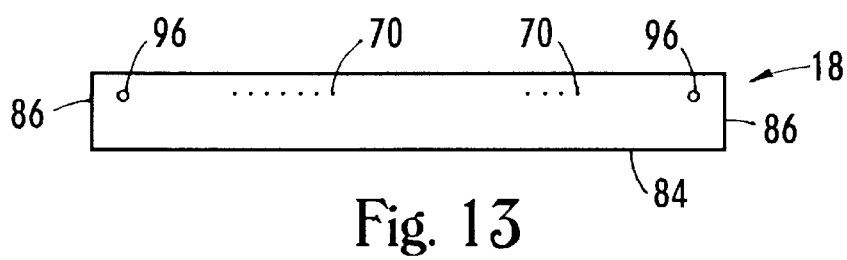
FIG. 13 is a bottom plan view of the holder of FIG. 11.
Figure 14:
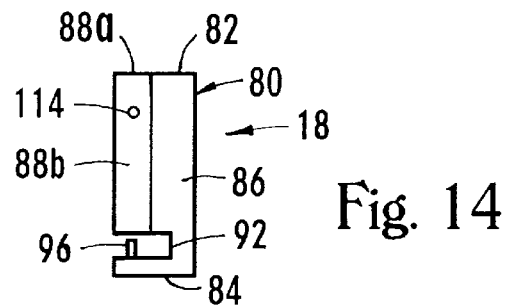
FIG. 14 is a side plan view of the holder of FIG. 11.
Figure 15:
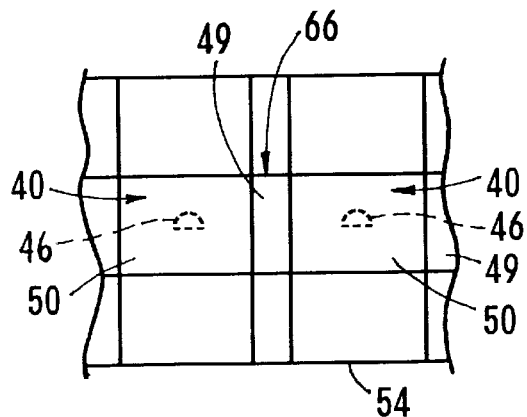
FIG. 15 is a cutaway view of the interface taken on line 15—15 of FIG. 8 with the capillary area shown in phantom.

In yet another embodiment shown in FIG. 10, a plurality of receptacles 40 can be made of a single piece or strip of liquid permeable medium which substantially resists or inhibits the flow of the ionic fluid 44 (not shown in FIG. 10) laterally between the adjacent receptacles 40. Thus, the liquid permeable medium resists the flow of ionic fluid transversely between the adjacent capillary areas 46. A suitable liquid permeable medium is sold by Nucleopore, Corporation located in Pleasanton, Calif., under the trademark Nucleopore.

In the embodiments shown in the Figures, the interface 14 is shaped similar to a rectangular strip and each receptacle 40 includes an upper surface 50, a lower surface 52 and edge surfaces 54.

The liquid permeable medium for each receptacle 40 is sufficiently liquid permeable to retain the ionic fluid 44. Further, the liquid permeable medium must be sufficiently compliant to form a fluid connection with the capillary opening 32 and compensate for any misalignment between the liquid permeable medium and the capillary opening 32. Typically, each liquid permeable medium is a piece of filtration membrane made from glass fiber filters, nylon or cellulose paper. A suitable liquid permeable medium is sold by Whatman International Ltd, in Maidstone, England under the designation C3353.

Alternately, the liquid permeable medium for each receptacle 40 could be a piece of membrane which separates plasma components from red blood cells such as that sold by Pall Biosupport Division of Port Washington, N.Y. under the trademark HEMADYNE or Primecare Diagnostics BV, located at 7602 KK 289 Almelo NL. In this embodiment, a blood specimen (not shown) can be deposited directly onto the liquid permeable medium. The liquid permeable medium separates the plasma for testing inside the capillary 12.

Figure 17:
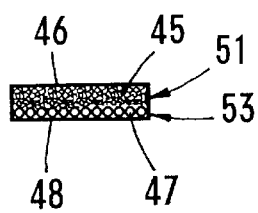
FIG. 17 is a side plan view of a receptacle having features of the invention.

Referring to FIG. 17, the liquid permeable medium for each receptacle 40 can include a fine pores area 45 proximate the capillary area 46 and coarse pores area 47 away from the capillary area 46. The size of the pores in fine pores area 45 is smaller than the size of the pores in the coarse pores area 47. In this version, the capillary area 46 would remain wet because of the capillary action of the fine pores area 45 while the coarse pores areas 47 would act as a buffer for excess ionic fluid 44. This would ensure that there is a good electrical path through the liquid permeable medium between the electrical conductor 16 and capillary opening 32 while deterring fluid flow between separated receptacles 40.

A suitable liquid permeable medium having graded porosity can be made from polyvinylidene fluoride ($PVF_2$) which has laminated graded pores. Alternately, the liquid permeable medium can be made from first and second parts 51, 53 jointed together. The first part 51 can be made of nylon having fine pores while the second part 53 can be made of cellulose paper having coarse pores.

Figure 18:
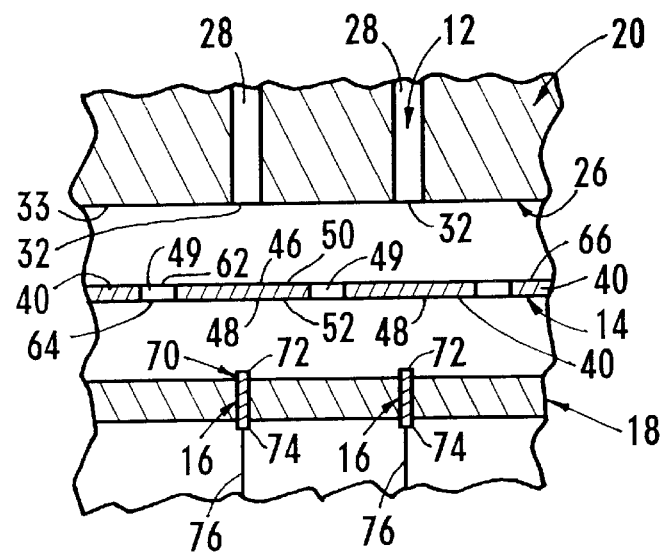
FIG. 18 is an exploded, cutaway view taken on line 18 of FIG. 1.

Referring to FIGS. 1 and 18, a single receptacle 40 can be used to connect one electrical conductor 16 to one capillary opening 32. In this version, the receptacles 40 are spaced so that a single capillary area 46 is placed in fluid communication with each of the capillary openings 32. Thus, the spacing and number of receptacles 40 depends upon the design of the capillary 12.

Also as shown in FIG. 1, the interface 14 can include extra receptacles 40 which are not connected to a capillary opening 32.

Alternatively, a single receptacle 40 can be used to connect one electrical conductor 16 to two or more capillary openings 32. In this version, a single receptacle 40 can include two or more capillary areas 46 aligned and in fluid communication with two or more capillary openings 32. Further, the two or more capillary openings 32 will be subject to the same electrical potential. This is particularly useful for common buffer inlets or waste outlets.

Referring to FIGS. 7–10 and 15, the capillary area 46 is a portion of the upper surface 50 of the receptacle 40. The capillary area 46 is substantially planar and typically has a cross-sectional size and shape which is at least as large as the capillary opening 32. Preferably, the capillary area 46 is slightly larger than the capillary opening 32 to allow for any misalignment. The capillary area 46 can be the entire upper surface 50 of the receptacle 40 or as shown in phantom in FIG. 15, the capillary area 46 can have a cross-sectional shape and size which corresponds to the cross-sectional shape and size of the capillary opening 32.

In the embodiments shown in the FIGS. 7–10, the capillary areas 46 are all substantially coplanar to facilitate interaction with capillary openings 32 which are coplanar.

Each conductor area 48 contacts one of the electrical conductors 16 and forms an electrical connection with the electrical conductor 16. Thus, the design of conductor area 48 varies according to the design of the electrical conductor 16. The conductor area 48 is substantially planar and typically has a cross-sectional size and shape which is at least as large as the cross-sectional shape of the portion of the electrical conductor 16 which contacts the conductor area 48. Preferably, each conductor area 48 is also slightly larger than the electrical conductor 16 to allow for misalignment.

Figure 16:
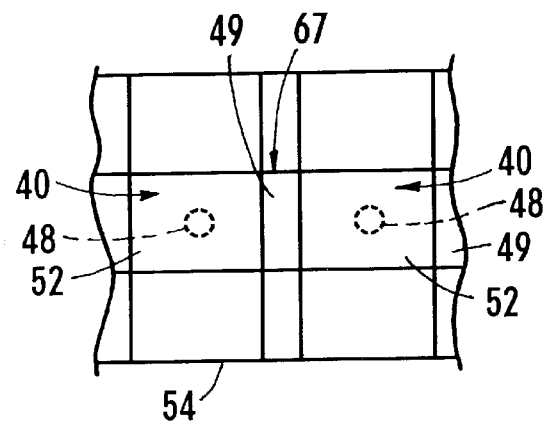
FIG. 16 is a cutaway view of the interface taken on line 16—16 of FIG. 8 with the conductor area shown in phantom.

Referring to FIG. 16, the conductor area 48 can be a portion of a lower surface 52 which contacts one of the electrical conductors 16. The conductor area 48 can be the entire lower surface 52 of the receptacle 40 or as shown in phantom in FIG. 16, the conductor area 48 can have a cross-sectional shape and size which corresponds to the cross-sectional shape and size of the electrical conductor 16. Alternately, the conductor area 48 can be a portion (not shown) of the upper surface 50 or a portion (not shown) of one of the edge surfaces 54 of the receptacles 40.

The dimensions of each receptacle 40 depend upon the material utilized in the liquid permeable medium and the design of the capillary 12. In the embodiment shown in FIGS. 7 and 8, each receptacle 40 is a rectangular strip of filter paper which is approximately 0.010 inches thick, 0.067 inches wide and 0.420 inches long.

Figure 5:
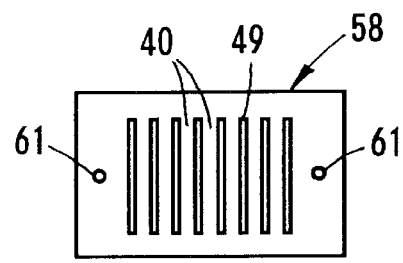
FIG. 5 is a top plan view of a continuous piece of liquid permeable medium prior to assembly to the support of FIG. 4.

As shown in FIG. 5, a plurality of receptacles 40 can be formed by die cutting the inhibitors 49, i.e., spaces in a sheet 58 of liquid permeable medium. In the embodiment, each space is about 0.031 inches wide. Alternately, as described previously, the inhibitor 49 could be a flow retarding boundary impregnated into the liquid permeable medium by printing.

The sheet 58 can include a sheet aligner 61 for aligning the sheet 58 with the support 42 during assembly and/or aligning the interface 14 in the CE system 10. As shown in FIG. 5, the sheet aligner 61 can be a pair of small apertures in the sheet 58.

Figure 6:
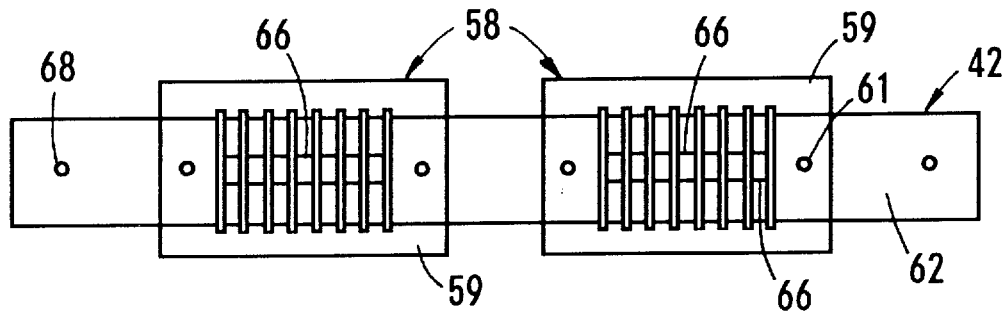
FIG. 6 is a top plan view of a pair of continuous pieces of FIG. 5 retained by the support of FIG. 4.

Referring to FIG. 6, during assembly of interface 14, the sheet 58 of liquid permeable medium can be secured to the support 42 with edges 59 of the sheet 58 exposed. FIG. 7 shows the sheet 58 of liquid permeable medium with the exposed edges 59 removed to form the spaced apart receptacles 40.

The support 42 retains the plurality of receptacles 40. Preferably, the support 42 is selectively attachable to the capillary 12 to allow for easy installation and washing of the capillary 12.

Referring to FIG. 8, the support 42 can include an upper piece of tape 62 and a lower piece of tape 64 which sandwich the receptacles 40 together. The upper and lower tape 62, 64 are made of any material which does not adversely affect or is not adversely affected by the ionic fluids 44 utilized in the experiment.

A piece of about 0.002 inch thick, substantially clear polyester which includes a pressure sensitive adhesive such as an acrylic adhesive makes an excellent support 42. In this embodiment, the upper and lower tapes 62, 64 are bonded together and to the plurality of receptacles 40 by applying about ten P.S.I. for about ten seconds. Alternately, the first and second tapes 62, 64 can be made from any tape which is substantially nonporous and which does not adversely affect the ionic fluid 44.

Referring to FIGS. 4, 6, 7, 9 and 10, the upper tape includes a pair of upper tape apertures 66 which expose and allow for contact between the capillary areas 46 and the capillary openings 32. Similarly, as shown in FIG. 16, the lower tape 64 includes lower apertures 67 which allow for contact between the conductor areas 48 and the electrical conductors 16.

The size and shape of the tape apertures 66, 67 vary according to the number and size of capillary openings 32. In the embodiment shown in the figures, the tape apertures 66, 67 are rectangular shaped and are about 0.124 inches wide by about 0.724 inches long.

Further, the support 42 can also include an interface aligner 68 for aligning the sheet 58 of liquid permeable medium during assembly with the support 42 and/or aligning the interface 14 in the CE system 10. In the embodiment shown in the figures, the interface aligner 68 is a number of apertures having a cross-sectional diameter of about 0.064 inches.

Alternately, the support 42 can be an adhesive such as the acrylic adhesive trademarked as Fas Tape 1111 manufactured by Avery Dennison Specialty Tape Division of Painesville, Ohio, which adheres each of the receptacles 40 to the housing 20. However, this method is not preferred since the interface 14 is difficult to replace and/or remove between tests.

The ionic fluid 44 is electrically conductive and is retained by the receptacles 40. The ionic fluid 44 provides the electrical path between the capillary opening 32 and the electrical conductor 16. The ionic fluid 44 can be the sample being tested, an analytical reagent such as glucose oxidase, gels for separation of DNA such as polyacrylamide, labeling reagents such as fluorescein, a separation buffer such as 20 mM boric acid in 50 mM tris(hydroxymethyl)aminomethane or an alternate fluid. Depending upon the requirements of the experiment, a different ionic fluid 44 can be disposed in each of the receptacles 40.

A sufficient amount of ionic fluid 44 is disposed in each receptacle 40 to establish the electrical path between the capillary area 46 and conductor area 48. However, too much ionic fluid 44 can cause fluid flow between adjacent receptacles 40. Thus, the amount of ionic fluid 44 varies according to the size and material used in the liquid permeable medium. For the embodiment shown in FIGS. 7 and 8, between about one to ten microliters is sufficient to establish the electrical path. The ionic fluid 44 can be distributed to the liquid permeable medium by wicking with a pipette 69 as shown in FIG. 8 or ink jet printing.

The design of the electrical conductors 16 varies according to the design of the CE system 10. For example, as shown in FIG. 1, each electrical conductor 16 is a pin which fits tightly into and is retained by a conductor aperture 70 in the holder 18.

In the embodiment shown in FIG. 1, each pin has a first tip 72 which contacts the conductor area 48 and a second tip 74 which is connected to a connection wire 76. In other versions, the first tip 72 can alternately contact a portion of the upper surface 50, lower surface 52 or edge surfaces 54 of the receptacle 40. The connection wires 76 are electrically connected to an electrical supply 78.

Alternately, the plurality of electrical conductors 16 can be a printed circuit board (not shown) contacting the plurality of conductor areas 48 or can be directly attached to the conductor areas 48 with printing or an adhesive.

The electrical conductors 16 can be made from any conductive material which is not adversely affected or adversely affects the ionic fluid 44. For example, the pins shown in FIGS. 1 and 18 can be made of stainless steel or gold plated phosphor bronze.

The holder 18 selectively retains the interface 14 in fluid communication with the capillary openings 32 and in contact with the electrical conductors 16. Thus, the design of the holder 18 also varies according to the design of the CE system 10.

Referring to FIGS. 11–14, the holder 18 includes a substantially rectangular frame 80 having a first member 82, an opposed, spaced apart, and substantially parallel second member 84 and a pair of opposed side members 86 which cooperate to retain the first and second members 82, 84. The first and second members 82, 84 are spaced apart a sufficient distance to retain the housing 20 and the interface 14 therebetween.

The first member 82 includes a first protruding lip 88a and each of the opposed side members 86 include a side protruding lip 88b to receive and retain the housing 20. The protruding lips 88a, 88b extend outwardly from the housing 20 and are an integral part of the first member 82 and the side members 86. The side members 86 also include a rectangular shaped slot 92 proximate the second member 84 for receiving the interface 14.

The second member 84 includes a plurality of conductor apertures 70, each sized to receive and retain an electrical conductor 16. In the embodiment shown in the figures, the holder 18 includes eleven conductor apertures 70, each having a cross-sectional diameter of about thirty thousandths (0.030) of an inch. However, the number, spacing and size of the conductor apertures 70 depends upon the number, spacing and size of the electrical conductors 16 and the capillary 12.

The second member 58 also includes a number of alignment members 96, for aligning the interface 14 with the electrical conductors 16, and the capillary openings 32. In the embodiment shown in the figures, the alignment members 96 are pins having a cross-sectional diameter of about 0.070 inches. The alignment members 96 cooperate with the interface aligner 68 to align the components of the CE system.

Preferably, the holder 18 also includes a housing aligner 110 which aligns the housing 20 with the holder 18. In the embodiment shown in the Figures, the housing aligner 110 is a pair of externally threaded members 112. Each externally threaded member 112 threads into an internally threaded surface 114 in each side member 86 of the holder 18. Alternately, the housing aligner 110 can be furnished with pins (not shown) which extend away from the housing 20 and fit into apertures (not shown) in the second member 84.

The holder 18 includes a pressure inducer 90 positioned between the first and second members 82, 84. The pressure inducer 90 expands to press the housing 20 and interface 14 together. The pressure inducer 90 can be one or more springs which extend downwardly from the first member 82. The springs force the housing 20 towards the second member 84 to maintain contact between the capillary openings 32, the interface 14 and the electrical conductors 16.

The holder 18 can be made of molded, black ABS or any material which is strong enough to retain the housing 20 and the interface 14 and is not a good conductor of electricity.

In operation, the plurality of electrical conductors 16 extend through the conductor apertures 70. The receptacles 40 of the interface 14 are wetted with the ionic fluid 44 and attached to the holder 18. These ionic fluids may be different at different receptacles. The sample and/or sample support medium can be added to the capillary 12 with a syringe (not shown) or added directly to the receptacles 40 with a pipette 69 or the sample support medium may replace one or more of the receptacles 40.

Subsequently, the housing 20 is attached to the holder 18. The alignment members 96 align the interface 14 with the capillary openings 32 and the electrical conductors 16. The pressure inducer 90 forces the capillary openings 32 against the interface 14 and the interface 14 against the plurality of electrical conductors 16.

An electrical potential is supplied by the electrical supply 78 to electrical conductors 16. The ionic fluid 44 in the receptacles 40 create an electrical path between the corresponding electrical conductors 16 and capillary opening 32. Further, the ionic fluid 44 in the receptacles 40 begins to migrate in the capillary 12.

As the ionic fluid 44 migrates in the capillary 12, the sample components begin to separate and pass a window section (not shown) of the capillary 12. An excitation source (not shown), such as a laser, is used to induce fluorescence of the separated components of the sample and such fluorescence is then detected by a collector for detection in a manner known to those skilled in the art. As provided in the Glass Chips article which has been incorporated herein by reference, a suitable laser is Model 532 AP, sold by Omnichrome and a suitable collector is the Hamamatsu R1477 photo multiplier tube.

Since the capillary openings 32 are manufactured simultaneously with the channels 28 and the interface 14 is made substantially of a liquid permeable medium, a capillary 12 having a plurality of capillary openings 32 can be interfaced with a plurality of electrical conductors 16 easily and relatively inexpensively.

Further, since the interface 14 is easily removed, there is less chance of diffusion of components between experiments and capillaries can be readily flushed without the fear of backwash.

While the present invention has been described in considerable detail with reference to certain preferred versions, other versions are possible. For example, the pressure inducer 90 can be a pair of externally threaded members (not shown) which are adjustably threaded into internally threaded apertures (not shown) in the first member 82 or a piece of rubber (not shown) disposed between the first member 82 and the housing 20. Therefore, the spirit and scope of the appended claims should not be limited to the description of those preferred versions which are contained herein.

What is claimed is:

1. A device for analysis of a fluid, the device comprising:
    (a) a substantially planar, substantially transparent housing having an interface surface which is located on an external side of the housing; and
    (b) a channel disposed within the housing, the channel being adapted for transporting the fluid during chemical analysis, the channel having a substantially constant cross-sectional area throughout the length of the channel;
    wherein the channel includes at least one capillary opening which extends through the interface surface of the housing.

2. The device of claim 1 further including a plurality of capillary openings, at least two of the capillary openings being substantially coplanar.

3. The device of claim 1 wherein the housing comprises (i) a substantially planar channel plate having an interface surface and an upper surface and (ii) a substantially planar cover plate sealed over the upper surface of the channel plate with an interface surface of the cover plate substantially aligned and substantially coplanar with the interface surface of the channel plate.

4. A capillary electrophoretic system comprising:
    (a) the device of claim 1;
    (b) an electrical conductor; and
    (c) an interface adapted for electrically connecting the capillary opening and the electrical conductor, the interface contacting the capillary opening and being in fluid communication with the capillary opening.

5. The device of claim 1 wherein the channel has a cross-sectional area of between approximately one hundred to five thousand micrometers squared.

6. A capillary electrophoretic system comprising:
    (a) a device comprising (i) a channel disposed in a substantially planar housing having an interface surface, and (ii) at least two capillary openings in fluid communication with the channel which extend through the interface surface of the housing;
    (b) at least two electrical conductors; and
    (c) an interface comprising at least two receptacles for receiving an ionic fluid, each receptacle having a capillary area and a conductor area separated by a liquid permeable medium, the liquid permeable medium including a plurality of pores which are adapted to retain a portion of the ionic fluid, the receptacles being spaced apart from each other a sufficient distance so that the capillary area of each receptacle is connected in fluid communication with one of the capillary openings and the receptacles being positioned so that at least two of the capillary areas are substantially coplanar;
    wherein an electrical path is established between the capillary area and conductor area of each receptacle without establishing an electrical path between at least two of the receptacles.

7. The capillary electrophoretic system of claim 6 wherein at least two of the receptacles comprise a continuous piece of liquid permeable medium which substantially inhibits the flow of liquid laterally between at least two of the receptacles, wherein the liquid permeable medium includes a plurality of pores.

8. The capillary electrophoretic system of claim 6 comprising an inhibitor for substantially inhibiting the flow of ionic fluid between at least two of the receptacles.

9. The capillary electrophoretic system of claim 8 wherein the inhibitor is an area between at least two receptacles which does not contain a liquid permeable medium having pores.

10. The capillary electrophoretic system of claim 8 wherein the inhibitor is a substantially hydrophobic barrier disposed in a liquid permeable medium between at least two receptacles.

11. The capillary electrophoretic system of claim 8 wherein each receptacle comprises an individual piece of liquid permeable medium having pores and the inhibitor comprises an area between at least two of the receptacles which does not contain a liquid permeable medium having pores.

12. The capillary electrophoretic system of claim 8 wherein at least two of the receptacles comprises an interconnected piece of liquid permeable medium having pores and the inhibitor comprises a substantially hydrophobic barrier disposed between at least two of the receptacles.

13. The capillary electrophoretic system of claim 6 wherein the housing is substantially transparent and includes a front surface which is substantially perpendicular to the interface surface and wherein, the channel is substantially parallel to the front surface of the housing and is adapted for transporting a fluid during capillary electrophoresis.

14. A method for making a device which is useful for an analysis of a fluid, the method comprising the steps of:
(a) forming a channel in an upper surface of a substantially planar, substantially transparent channel plate, the channel being adapted for transporting a fluid during capillary electrophoresis and having at least two, substantially coplanar capillary openings which extend through an external interface surface of the channel plate, the interface surface being substantially perpendicular to the upper surface, the channel having a substantially constant cross-sectional area throughout the length of the channel; and
(b) substantially sealing a substantially planar, substantially transparent cover plate over the upper surface of the channel plate.

15. The method of claim 14 wherein the step of substantially sealing the cover plate over the upper surface of the channel plate includes the step of substantially aligning the interface surface of the channel plate with an interface surface of the cover plate so that the interface surface of the cover plate and the interface surface of the channel plate are substantially coplanar.

16. The method of claim 14 wherein the step of forming a channel includes the step of forming a channel having a cross-sectional area of between approximately one hundred to five thousand micrometers squared.

17. A device for capillary electrophoresis, the device comprising:
a substantially planar housing having an interface surface which is located on a side of the housing; and
a capillary disposed in the housing, the capillary including two interconnected channels, each of the channels including a capillary opening which extends through the interface surface of the housing, each channel having a substantially constant cross-sectional area throughout the length of each channel.

18. The device of claim 17 wherein the housing is substantially transparent and include a front surface which is substantially perpendicular to the interface surface, wherein, the plurality of channels extend substantially parallel to the front surface.

19. An interface adapted for electrically connecting first and second capillary openings in a housing, the interface comprising:
first and second receptacles, each of the receptacles including a capillary area, a conductor area and a liquid permeable medium which receives an ionic fluid for establishing a separate electrical path between the capillary area and the conductor area for each receptacle, the liquid permeable medium having a plurality of pores which are adapted to retain a portion of the ionic fluid, the receptacles being spaced apart from each other a sufficient distance so that the capillary area of each receptacle is adapted to be connected in fluid communication with one of the capillary openings.

20. The interface of claim 19 including an inhibitor for substantially inhibiting the flow of ionic fluid between the first and second receptacles, the first and second receptacles being positioned so that the capillary area of each receptacle is substantially coplanar.

21. The interface of claim 20 wherein the inhibitor is an area between the first and second receptacles which does not contain a liquid permeable medium having pores.

22. The interface of claim 20 wherein the inhibitor is an area between the first and second receptacles which does not contain a liquid permeable medium having pores.

23. The interface of claim 20 wherein the inhibitor is a substantially hydrophobic barrier disposed between the first and second receptacles.

24. The interface of claim 20 wherein each receptacle comprises an individual piece of liquid permeable medium and the inhibitor comprises an area between the first and second receptacles which does not contain a liquid permeable medium having pores.

25. The interface of claim 20 wherein the interface further comprises a support which secures the first and second receptacles together.

26. The interface of claim 25 wherein the support includes an interface aligner for aligning the capillary areas with the capillary openings.

27. The interface of claim 19 wherein at least one of the receptacles includes a fine pores area positioned proximate the capillary area and a coarse pores area.

28. A capillary electrophoretic system comprising:
(a) a device comprising (i) a channel disposed in a housing having an interface surface, the channel being adapted for transporting a fluid during capillary electrophoresis, and (ii) first and second capillary openings in fluid communication with the channel which extend through the interface surface of the housing;
(b) at least two electrical conductors; and
(c) the capillary interface of claim 19 electrically connecting each of the capillary openings to one of the electrical conductors.

29. The capillary electrophoretic system of claim 28 wherein the housing is substantially transparent and comprises (i) a substantially planar channel plate having an interface surface and an upper surface and (ii) a substantially planar cover plate sealed over the upper surface of the channel plate with an interface surface of the cover plate substantially aligned and substantially coplanar with the interface surface of the channel plate.

30. The capillary electrophoretic system of claim 28 wherein the capillary areas are adapted to be selectively moved into and out of fluid communication with the capillary openings.

31. The capillary electrophoretic system of claim 28 comprising a holder for selectively retaining the capillary areas in fluid communication with the capillary openings, the holder comprising (i) first and second members, spaced apart a sufficient distance to receive the housing and the interface therebetween and (ii) a pressure inducer adapted for pressing the interface surface of the housing and the interface together.

32. The capillary electrophoretic system of claim 28 wherein the capillary openings are spaced apart a distance which is substantially equal to "X" and the capillary areas are spaced apart a distance which is substantially equal to "X".

33. A capillary electrophoretic system comprising:
a device including (i) a substantially planar, substantially transparent housing having front surface and an interface surface and (ii) a channel extending substantially parallel to the front surface, the channel being adapted for transporting a fluid during capillary electrophoresis and including a capillary opening in fluid communication with the channel which extends through the interface surface of the housing;
an electrical conductor; and an interface including receptacle having a capillary area which is in fluid communication with the capillary opening and a conductor area which contacts the electrical conductor, the receptacle including a liquid permeable medium having a plurality of pores which receive an ionic fluid to establish an electrical path between the capillary area and conductor area.

34. The capillary electrophoretic system of claim 33 including a holder having a pressure inducer which is adapted for pressing the interface surface of the housing and the interface together.

35. A capillary electrophoretic system comprising:

a device for the analysis of a fluid, the device comprising: (i) a substantially planar, substantially transparent housing having an interface surface which is located on an external side of the housing; (ii) a channel disposed within the housing, the channel being adapted for transporting the fluid during chemical analysis; and (iii) at least one capillary opening in fluid communication with the channel which extends through the interface surface of the housing;

an electrical conductor; and an interface adapted for electrically connecting the capillary opening and the electrical conductor, the interface comprising a first receptacle having a liquid permeable medium for receiving an ionic fluid, the liquid permeable medium including pores which are adapted to retain a portion of the ionic fluid.

36. The capillary electrophoretic system of claim 35 wherein the capillary includes a second capillary opening and the interface includes at least a second receptacle, the first and second receptacles each comprising (i) a liquid permeable medium having a plurality of pores which are adapted to retain a portion of the ionic fluid and (ii) the first and second receptacles each including a co-planar capillary area connected in fluid communication with one of the capillary openings.

37. The capillary electrophoretic system of claim 36, wherein the interface further comprising an inhibitor for inhibiting the flow of ionic fluid between the receptacles.

38. A capillary electrophoretic system comprising:

a device for the analysis of a fluid, the device comprising: (i) a substantially planar, substantially transparent housing having an interface surface which is located on an external side of the housing; (ii) a channel disposed within the housing, the channel being adapted for transporting the fluid during chemical analysis; and (iii) at least one capillary opening in fluid communication with the channel which extends through the interface surface of the housing;

an electrical conductor;

an interface adapted for electrically connecting the capillary opening and the electrical conductor; and a holder for selectively retaining the interface in fluid communication with the capillary opening, the holder comprising (i) first and second members, spaced apart a sufficient distance to receive the housing and the interface therebetween and (ii) a pressure-inducer positioned between the first and second members which expands a sufficient distance to press the interface surface of the housing and the interface together.

* * * * *